US012171892B2

(12) United States Patent
Voss et al.

(10) Patent No.: US 12,171,892 B2
(45) Date of Patent: Dec. 24, 2024

(54) REDUCING MICROBIAL GROWTH ON PACKAGED TERMINAL AIR CONDITIONERS

(71) Applicant: Ecolab USA Inc., St. Paul, MN (US)

(72) Inventors: Peter Andrew Voss, Eagan, MN (US); Paul Dominic Christian, Apple Valley, MN (US); Teresa C Podtburg, Waconia, MN (US); Paul R. Kraus, Apple Valley, MN (US)

(73) Assignee: Ecolab USA Inc., St. Paul, MN (US)

( * ) Notice: Subject to any disclaimer, the term of this patent is extended or adjusted under 35 U.S.C. 154(b) by 578 days.

(21) Appl. No.: 17/325,398

(22) Filed: May 20, 2021

(65) Prior Publication Data

US 2021/0369890 A1 Dec. 2, 2021

Related U.S. Application Data

(60) Provisional application No. 63/031,912, filed on May 29, 2020.

(51) Int. Cl.
*F24F 8/22* (2021.01)
*A61L 2/10* (2006.01)
(Continued)

(52) U.S. Cl.
CPC ............ *A61L 2/10* (2013.01); *F28G 13/00* (2013.01); *F28G 15/003* (2013.01); *A61L 2202/11* (2013.01)

(58) Field of Classification Search
CPC .................................. F24F 8/22; A61L 2/10
See application file for complete search history.

(56) References Cited

U.S. PATENT DOCUMENTS 5,755,103 A 5/1998 Na et al.
6,524,529 B1 2/2003 Horton, III
(Continued)

FOREIGN PATENT DOCUMENTS

CN 1653305 A 8/2005
CN 101452358 A 6/2009
(Continued)

OTHER PUBLICATIONS

English Translation of Document ID No. KR 20180010824 provided by the European Patent Office website Espacenet.com: Kim Tae Young; Air Conditioner; Jan. 31, 2018 (Year: 2018).*
(Continued)

*Primary Examiner* — Kevin Joyner
(74) *Attorney, Agent, or Firm* — Shumaker & Sieffert, P.A.

(57) ABSTRACT

An antimicrobial lighting system is used to reduce microbial growth on surfaces in or on air conditioning and/or heating equipment. In some examples, antimicrobial light within one or more antimicrobial wavelength ranges is applied to inactivate one or more microorganisms on target surface(s) within or on a packaged terminal air conditioner (PTAC). The antimicrobial light may include light within a first antimicrobial wavelength range and/or light within a second antimicrobial wavelength range. The antimicrobial lighting system may include an array of individually controllable antimicrobial light segments. An array controller may individually control activation of the one or more antimicrobial light segments based on the status information or commands received from a PTAC controller or from an external computing device.

21 Claims, 6 Drawing Sheets

(51) Int. Cl.
*F28G 13/00* (2006.01)
*F28G 15/00* (2006.01)

(56) References Cited

U.S. PATENT DOCUMENTS

| | | | |
|---|---|---|---|
| 6,573,663 | B1 | 6/2003 | MacGregor et al. |
| 7,270,195 | B2 | 9/2007 | MacGregor et al. |
| 8,182,744 | B2 | 5/2012 | Mlodzinski et al. |
| 8,398,264 | B2 | 3/2013 | Anderson et al. |
| 8,581,882 | B2 | 11/2013 | Sohn et al. |
| 9,039,966 | B2 | 5/2015 | Anderson et al. |
| 9,700,641 | B2 | 7/2017 | Hawkins et al. |
| 9,839,706 | B2 | 12/2017 | Anderson et al. |
| 9,963,597 | B2 | 5/2018 | Aizenberg et al. |
| 10,232,066 | B2 | 3/2019 | Bailey |
| 10,773,690 | B2 | 9/2020 | Dellock et al. |
| 11,819,581 | B2 | 11/2023 | Kraus et al. |
| 2002/0189270 | A1 | 12/2002 | Stensrud et al. |
| 2004/0175290 | A1 | 9/2004 | Scheir et al. |
| 2006/0021375 | A1 | 2/2006 | Wetzel et al. |
| 2010/0303671 | A1 | 12/2010 | Bertrand |
| 2011/0216042 | A1 | 9/2011 | Wassvik et al. |
| 2012/0228645 | A1 | 9/2012 | Tu et al. |
| 2013/0224086 | A1 | 8/2013 | Stibich et al. |
| 2013/0291735 | A1* | 11/2013 | Livchak ............... F24F 1/0047 165/48.1 |
| 2014/0060096 | A1 | 3/2014 | Shur et al. |
| 2014/0060104 | A1 | 3/2014 | Shur et al. |
| 2014/0061509 | A1 | 3/2014 | Shur et al. |
| 2014/0079587 | A1 | 3/2014 | Dayton |
| 2014/0264076 | A1 | 9/2014 | Bettles et al. |
| 2014/0300581 | A1 | 10/2014 | Aurongzeb et al. |
| 2015/0182647 | A1 | 7/2015 | Ranta et al. |
| 2016/0271803 | A1 | 9/2016 | Stewart |
| 2016/0375161 | A1 | 12/2016 | Hawkins et al. |
| 2017/0095585 | A1 | 4/2017 | Smetona et al. |
| 2017/0100989 | A1 | 4/2017 | Chapaton et al. |
| 2017/0246331 | A1 | 8/2017 | Lloyd |
| 2017/0333582 | A1 | 11/2017 | Davis |
| 2017/0340761 | A1 | 11/2017 | Shur et al. |
| 2017/0368213 | A1 | 12/2017 | Mintie et al. |
| 2018/0023821 | A1 | 1/2018 | Kim et al. |
| 2018/0046166 | A1 | 2/2018 | Kumar et al. |
| 2018/0113066 | A1 | 4/2018 | Freitag et al. |
| 2018/0117189 | A1 | 5/2018 | Yadav et al. |
| 2018/0117190 | A1 | 5/2018 | Bailey |
| 2018/0117193 | A1 | 5/2018 | Yadav et al. |
| 2018/0124883 | A1 | 5/2018 | Bailey |
| 2018/0126021 | A1 | 5/2018 | Valentine et al. |
| 2018/0140727 | A1 | 5/2018 | Romo et al. |
| 2018/0154027 | A1 | 6/2018 | Anderson et al. |
| 2018/0243452 | A1 | 8/2018 | Hawkins et al. |
| 2018/0243453 | A1 | 8/2018 | Hawkins et al. |
| 2018/0345485 | A1 | 12/2018 | Sinnet et al. |
| 2019/0001930 | A1 | 1/2019 | Dellock et al. |
| 2019/0176338 | A1 | 6/2019 | Zito et al. |
| 2019/0298871 | A1 | 10/2019 | Dobrinsky |
| 2020/0205926 | A1 | 7/2020 | Keibel |
| 2020/0254122 | A1* | 8/2020 | Starkweather ............ A61L 2/10 |
| 2020/0289683 | A1 | 9/2020 | Christian et al. |
| 2021/0000991 | A1 | 1/2021 | Kraus et al. |
| 2021/0308317 | A1 | 10/2021 | Chen |

FOREIGN PATENT DOCUMENTS

| | | |
|---|---|---|
| CN | 101622016 A | 1/2010 |
| CN | 204121454 U | 1/2015 |
| CN | 104704067 A | 6/2015 |
| CN | 105142682 B | 12/2015 |
| CN | 105163605 B | 12/2015 |
| CN | 204864170 U | 12/2015 |
| CN | 105856259 A | 8/2016 |
| CN | 105879148 A | 8/2016 |
| CN | 105963730 A | 9/2016 |
| CN | 205747250 U | 11/2016 |
| CN | 106272467 A | 1/2017 |
| CN | 206085069 U | 4/2017 |
| CN | 206795846 U | 12/2017 |
| CN | 108068125 A | 5/2018 |
| CN | 207710799 U | 8/2018 |
| CN | 108606754 A | 10/2018 |
| CN | 108714884 A | 10/2018 |
| CN | 109065186 A | 12/2018 |
| CN | 106444564 B | 1/2019 |
| CN | 109131234 A | 1/2019 |
| CN | 109202939 A | 1/2019 |
| CN | 109276728 A | 1/2019 |
| CN | 109316612 A | 2/2019 |
| CN | 109431810 A | 3/2019 |
| CN | 109481707 A | 3/2019 |
| CN | 109481708 A | 3/2019 |
| DE | 102017209966 A1 | 12/2018 |
| EP | 3355940 A2 | 8/2018 |
| JP | 2015167470 A | 9/2015 |
| JP | 2018117586 A | 8/2018 |
| KR | 1499359 B1 | 3/2015 |
| KR | 1724447 B1 | 4/2017 |
| KR | 20180010824 A | 1/2018 |
| KR | 20190054955 A | 5/2019 |
| WO | 2003096387 A2 | 11/2003 |
| WO | 2006124211 A1 | 11/2006 |
| WO | 2014036080 A1 | 3/2014 |
| WO | 2015051024 A1 | 4/2015 |
| WO | 2014036080 A9 | 5/2015 |
| WO | 2017062260 A2 | 4/2017 |
| WO | 2018087171 A1 | 5/2018 |
| WO | 2018122009 A1 | 7/2018 |

OTHER PUBLICATIONS

Office Action from U.S. Appl. No. 16/818,138, dated May 24, 2022, 13 pp.

Advisory Action from U.S. Appl. No. 16/918,644, dated Apr. 17, 2023, 2 pp.

Response to Final Office Action dated Feb. 6, 2023 from U.S. Appl. No. 16/918,644, filed Apr. 4, 2023, 12 pp.

"Hubbell Lighting to Integrate Bacteria Suppressing Technology into Smart Luminaires," http://www.lightingdesignandspecification.ca/changing-scene/2322-hubbe, Jun. 1, 2018, 1 pp.

"Ice UV," retrieved from https://www.freshaireuv.com/ice-machines/ on Feb. 22, 2019, 5 pp.

"LG Electronics LP153HD3B Installation Guide," retrieved from manualzz.com/doc/4030343/lg-electronics-lp153hd3b-installation-guide on May 11, 2020, 2 pp.

"Light Fixture Kills Bacteria Safely, Continuously," Science Daily, Jun. 26, 2015, 2 pp.

"Single Color Outdoor Weatherproof LED Flexible Lightstrip Part No. WFLS-x," https://d114hh0cykhyb0.cloudfront.net/pdfs/WFLS-x.pdf, Apr. 21, 2014, 2 pp.

"Wireless LED 4 Channel EZ Dimmer Controller with Channel Pairing," https://www.superbrightleds.comjmoreinfojrgb-led-controllers/wireless-4-channelrgb-led-dimmer-receiver/3372/7141/#tab/Reviews, Jul. 17, 2018, 7 pp.

Endarko et al., "High-Intensity 405 nm Light Inactivation of Listeria Monocytogenes," Photochemistry and Photobiology, vol. 88, No. 5, Sep.-Oct. 2012, pp. 1280-1286.

Gunther et al., "The Effects of 405-nm Visible Light on the Survival of Campylobacter on Chicken Skin and Stainless Steel," Foodborne Pathogens and Disease, vol. 13, No. 5, May 2016, 6 pp.

Kim et al., "Antibacterial Effect and Mechanism of High-Intensity 405 ± 5 nm Light Emitting Diode on Bacillus Cereus, Listeria Monocytogenes, and *Staphylococcus aureus* Under Refrigerated Condition," Journal of Photochemistry and Photobiology B: Biology, vol. 153, Dec. 2015, pp. 33-39.

Kingsley et al., "Evaluation of 405-nm Monochromatic Light for Inactivation of Tulane Virus on Blueberry Surfaces," Journal of Applied Microbiology, vol. 124, No. 4, Apr. 2018, pp. 1017-1022.

Lacombe et al., "Reduction of Bacterial Pathogens and Potential Surrogates on the Surface of Almonds Using High-Intensity 405-nanometer light," Journal of Food Protection, vol. 79, No. 11, Nov. 2016, pp. 1840-1845.

(56) References Cited

OTHER PUBLICATIONS

MacLean et al., "High-Intensity Narrow-Spectrum Light Inactivation and Wavelength Sensitivity of *Staphylococcus aureus*," Federation of European Microbiological Societies, Jun. 16, 2008, pp. 227-232.
MacLean et al., "Sporicidal Effects of High-Intensity 405 nm Visible Light on Endospore-Forming Bacteria," Photochemistry and Photobiology, vol. 89, No. 1, Jan./Feb. 2013, pp. 120-126.
McDonald et al., "405 nm Light Exposure of Osteoblasts and Inactivation of Bacterial Isolates from Arthroplasty Patients: Potential for New Disinfection Applications?", European Cells and Materials, vol. 25, Mar. 7, 2013, pp. 204-214.
Murdoch et al., "Bactericidal Effects of 405nm Light Exposure Demonstrated by Inactivation of *Escherichia, Salmonella*, Shigella, Listeria, and*Mycobacterium* Species in Liquid Suspensions and on Exposed Surfaces," The Scientific World Journal, vol. 2012, Apr. 1, 2012, 8 pp.
Murdoch et al., "Inactivation of Campylobacter Jejuni by Exposure to High-Intensity 405-nm Visible Light," Foodborne Pathogens and Disease, vol. 7, No. 10, Oct. 2010, pp. 1211-1216.
Ramakrishnan et al., "Differential Sensitivity of Osteoblasts and Bacterial Pathogens to 405-nm Light Highlighting Potential for Decontamination Applications in Orthopedic Surgery," Journal of Biomedical Optics, vol. 9, No. 10, Oct. 2014, 8 pp.
U.S. Appl. No. 17/101,449, filed Nov. 23, 2020, by Finison.
U.S. Appl. No. 17/325,440, filed May 20, 2021, by Hatch et al.
Office Action from U.S. Appl. No. 16/918,644 dated Aug. 22, 2022, 14 pp.
Response to Office Action dated May 24, 2022 from U.S. Appl. No. 16/818,138, filed Aug. 24, 2022, 14 pp.
Notice of Allowance from U.S. Appl. No. 16/818,138 dated Oct. 20, 2022, 10 pp.
Response to Office Action dated Aug. 22, 2022 from U.S. Appl. No. 16/918,644, filed Nov. 22, 2022, 12 pp.
Final Office Action from U.S. Appl. No. 16/918,644 dated Feb. 6, 2023, 18 pp.
Notice of Allowance from U.S. Appl. No. 16/918,644 dated Jul. 14, 2023, 12 pp.
International Search Report and Written Opinion of International Application No. PCT/US2021/033313, mailed Aug. 27, 2021, 12 pp.
Response to Communication Pursuant to Rules 161(1) and 162 EPC dated Jan. 11, 2023, from counterpart European Application No. 21732718.8, filed Jun. 27, 2023, 14 pp.
Office Action from U.S. Appl. No. 18/494,121 dated May 16, 2024, 10 pp.
Response to Office Action dated Apr. 9, 2024 from U.S. Appl. No. 17/325,440, filed Jul. 5, 2024, 12 pp.
Office Action from U.S. Appl. No. 17/325,440 dated Apr. 9, 2024, 17 pp.
Superbrightleds.com, "180° optics improve visibility with wider area illumination LED Lighting for Everything Weatherproof LED Flexible Light Strip Single Color Outdoor", Apr. 21, 2014, 2 pp., Retrieved at: https://d114hh0cykhyb0.cloudfront.net/pdfs/WFLS-x.pdf.
Superbrightleds.com, "Wireless LED 4 Channel EZ Dimmer Controller w/ Channel Pairing | Super Bright LEDs", Jul. 17, 2018, 15 pp., Retrieved at: https://www.superbrightleds.com/moreinfo/rgb-led-controllers/wireless-4-channel-rgb-led-dimmer-receiver/3372/7141/#tab/Reviews.
Response to Office Action dated May 16, 2024 from U.S. Appl. No. 18/494,121, filed Aug. 6, 2024, 9 pp.

\* cited by examiner

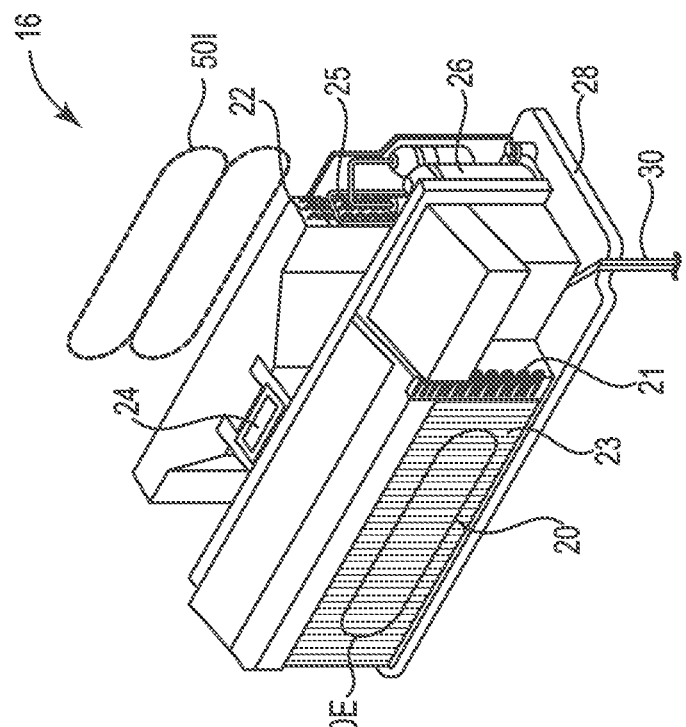
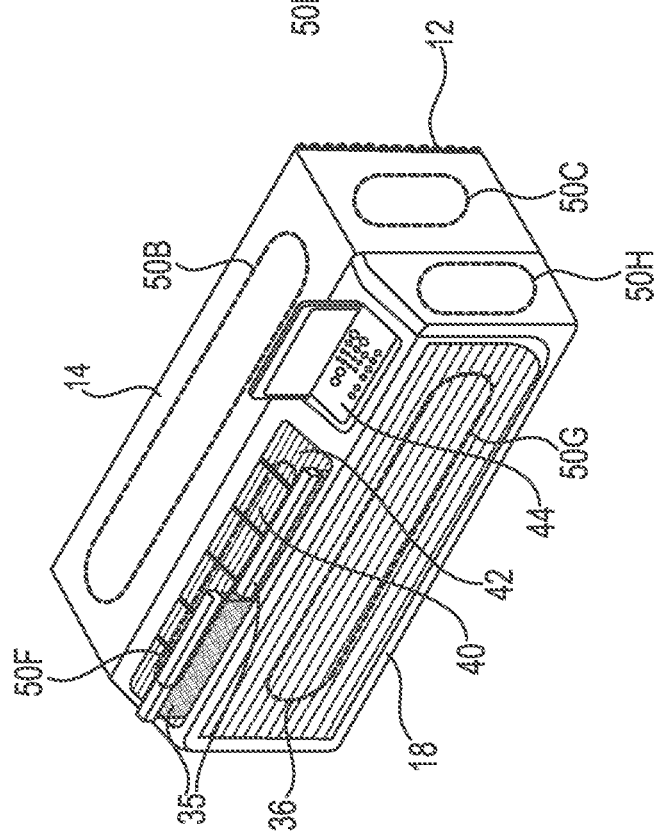

REDUCING MICROBIAL GROWTH ON PACKAGED TERMINAL AIR CONDITIONERS

This application claims the benefit of U.S. Provisional Application No. 63/031,912, titled, "REDUCING MICROBIAL GROWTH ON PACKAGED TERMINAL AIR CONDITIONERS", filed May 29, 2020, the entire content of which is incorporated herein by reference.

BACKGROUND

A Packaged Terminal Air Conditioner ("PTAC") is a type of ductless, self-contained heating and/or air conditioning system designed to heat and/or cool a single living space. As such, PTACs are commonly found in hotels, senior housing facilities, hospitals, apartment buildings, and other settings where environmental control of a single room or other relatively small area is desired. PTACs are typically installed through an exterior wall and operate by extracting condensate water from the interior air and draining or evaporating the water to the exterior environment.

Presence of water and water vapor inside or on the exterior surfaces of a PTAC may result in undesirable growth of microorganisms within or around the PTAC. For example, environmental microorganisms that may accumulate in or around the PTAC and that may be inactivated using the decontamination devices and methods of the present disclosure include, but are not limited to, *Listeria monocytogenes*, *Legionella* sp., *Salmonella* sp., *Pseudomonas* sp., *Acinetobacter* sp., *Moraxella* sp., *Alcaligenes* sp., *Flavobacterium* sp., *Acremonium* sp., *Eurobasidium* sp., *Exophiala* sp., *Sporobolomyces* sp., *Rhodotorula* sp., and the like, varieties of fungus, algae, mold and/or slime.

SUMMARY

In general, the disclosure is directed to systems and/or methods in which antimicrobial light is used to reduce or mitigate microbial growth in or on air conditioning and/or heating equipment. In some examples, the disclosure is directed to systems and/or methods in which antimicrobial light within one or more antimicrobial wavelength ranges is applied to inactivate one or more microorganisms on target surface(s) within or on a packaged terminal air conditioner (PTAC). Application of the antimicrobial light may improve PTAC hygiene and reduce unpleasant odors associated with the accumulation of mold, slime and other microorganisms in and around the PTAC. In some examples, the systems and/or methods of the present disclosure may help maintain microbial growth below acceptable levels and extend the time needed between PTAC cleaning procedures.

In one example, the disclosure is directed to a system comprising a lighting array including one or more antimicrobial lighting segments, each antimicrobial lighting segment including one or more light source elements, wherein each light source element emits antimicrobial light at a wavelength and irradiance sufficient to inactivate one or more microorganisms on a target surface associated with a heating and/or air conditioning unit; and a lighting array controller comprising: one or more processors; and a data storage device comprising instructions that when executed by the one or more processors cause the one or more processors to: receive one or more signals usable to determine status information concerning the heating and/or air conditioning unit; and individually control each antimicrobial lighting segment based on the determined status information concerning the heating and/or air conditioning unit.

The status information concerning the heating and/or air conditioning unit may include a current operational mode, and wherein the current operational mode includes one of a cooling mode, a heating mode, a fan only mode, or a sleep mode. The heating and/or air conditioning unit may include a packaged terminal air conditioner (PTAC). The one or more signals usable to determine status information concerning the heating and/or air conditioning unit may include a signal indicative of whether the room is occupied. The one or more processors may individually control each antimicrobial lighting segment based on whether the room is occupied. The one or more processors may deactivate each antimicrobial light segment when the room is occupied. The signal indicative of whether the room is occupied may be received from a room occupancy sensor or a door sensor. The signal indicative of whether the room is occupied may be received from a computing device. The computing device may include a hotel reservation system.

The one or more processors may control each antimicrobial light segment based on the determined status information by activating a first set of the antimicrobial lighting segments and deactivating a second set of the antimicrobial lighting segments. The one or more antimicrobial lighting segments may be individually controllable such that each lighting segment may be independently activated at a first, high setting, a second, modified setting, or a third, deactivated setting. The one or more antimicrobial lighting segments may be disposed within the heating and/or air conditioning unit to direct light at the wavelength and irradiance sufficient to inactivate one or more microorganisms toward one or more target surfaces inside the heating and/or air conditioning unit. The target surfaces may include one or more of an evaporator coil surface, an evaporator fin surface, a condenser coil surface, an air filter surface, an air intake surface, an air discharge surface, a wall sleeve surface, a base pan surface, a compressor surface, or an exterior grille surface.

Each antimicrobial lighting segment may include a substrate and a plurality of light-emitting diode (LED) elements. Each antimicrobial lighting segment may include a substrate and a plurality of light-emitting diode (LED) elements, and each LED element may emit antimicrobial light within a first wavelength range of about 380-420 nanometers and having a peak wavelength of about 405 nanometers. The plurality of LED elements may be arranged in a linear pattern on the substrate. The plurality of LED elements may be arranged in a grid pattern on the substrate. The substrate may be one of a flexible substrate or a rigid substrate.

Each antimicrobial lighting segment may include a substrate and a plurality of light-emitting diode (LED) elements, wherein one or more of the LED elements emit light within a first antimicrobial wavelength range of about 380-420 nanometers, and one or more of the LED elements emit light within a second antimicrobial wavelength range of about 200-280 nanometers.

Each antimicrobial lighting segment may include a substrate and a plurality of light-emitting diode (LED) elements, wherein one or more of the LED elements emit light within a first antimicrobial wavelength range of about 380-420 nanometers and one or more of the LED elements emit light within a second antimicrobial wavelength range, wherein the second antimicrobial wavelength range includes at least one of ultraviolet A (UVA) light within a wavelength range of 315-400 nm, ultraviolet B (UVB) light within a wavelength range of 280-315 nm or ultraviolet C (UVC) light within a wavelength range of 200-280 nm.

In another example, the disclosure is directed to a method comprising disposing a lighting array including one or more antimicrobial lighting segments, each antimicrobial lighting segment including one or more light source elements, wherein each light source element emits light at a wavelength and irradiance sufficient to inactivate one or more microorganisms on at least one target surface associated with a heating and/or air conditioning unit; receiving one or more signals usable to determine status information concerning the heating and/or air conditioning unit; and individually controlling each antimicrobial lighting segment based on the determined status information concerning the heating and/or air conditioning unit.

Each antimicrobial lighting segment may include a substrate and a plurality of light-emitting diode (LED) elements, and wherein one or more of the LED elements emit light within a first antimicrobial wavelength range of about 380-420 nanometers and having a peak wavelength of about 405 nanometers. Each antimicrobial lighting segment may include a substrate and a plurality of light-emitting diode (LED) elements, wherein one or more of the light source elements emit light within a second antimicrobial wavelength range of about 200-280 nanometers.

The details of one or more examples are set forth in the accompanying drawings and the description below. Other features and advantages will be apparent from the description and drawings, and from the claims.

BRIEF DESCRIPTION OF DRAWINGS

FIGS. 2A and 2B are more detailed schematic diagrams of an assembled PTAC and PTAC unit, respectively, with multiple antimicrobial light segments installed for microbial inactivation on target surfaces in accordance with the present disclosure.

DETAILED DESCRIPTION

Figure 1:
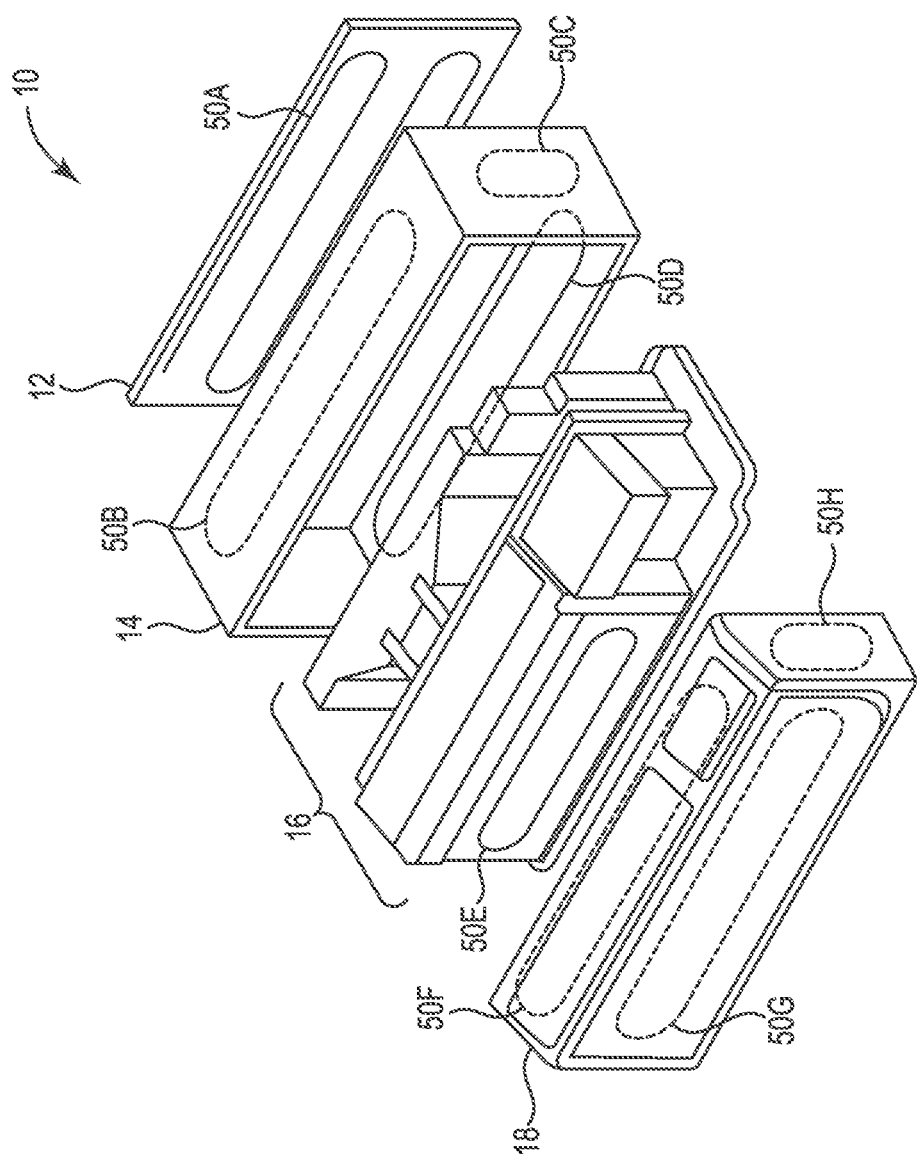
FIG. 1 shows an exploded schematic diagram of an example packaged terminal air conditioner (PTAC) with multiple antimicrobial light segments installed for microbial inactivation on target surfaces in accordance with the present disclosure.

In general, the disclosure is directed to systems and/or methods in which antimicrobial light is used to reduce microbial growth on surfaces in or on air conditioning and/or heating equipment. In some examples, the disclosure is directed to systems and/or methods in which antimicrobial light within one or more antimicrobial wavelength ranges is applied to inactivate one or more microorganisms on target surface(s) within or on a packaged terminal air conditioner (PTAC).

The antimicrobial light may include light within a first antimicrobial wavelength range of 380-420 nanometers (nm), and/or light within a second antimicrobial wavelength range, such as ultraviolet light within a wavelength range of 10-400 nanometers (nm). In some examples, the antimicrobial light within the first wavelength range has a peak wavelength of about 405 nm. In some examples, the antimicrobial light within the second wavelength range may include ultraviolet A (UVA) light within a wavelength range of 315-400 nm, ultraviolet B (UVB) light within a wavelength range of 280-315 nm and/or ultraviolet C (UVC) light within a wavelength range of 200-280 nm. Application of the antimicrobial light may improve PTAC hygiene and reduce unpleasant odors associated with the accumulation of mold, slime and other microorganisms on surfaces in and around the PTAC. In some examples, the systems and/or methods may help extend the time needed between PTAC cleaning procedures to maintain microbial growth below acceptable levels.

Although the disclosure will generally discuss antimicrobial lighting for reduction of microbial growth in or on PTACs, it shall be understood that the antimicrobial lighting arrays of the present disclosure may also be used to reduce microbial growth in other types of heating and/or air conditioning equipment, and that the disclosure is not limited in this respect. For example, the antimicrobial lighting arrays may also be used to reduce microbial growth in central air conditioning units, window air conditioning units, ductless/mini-split air conditioning units, portable air conditioning units, hybrid (e.g., heating and cooling) air conditioners, geothermal air conditioners, and any other air conditioning equipment that is susceptible to microbial growth or that could benefit from mitigation or reduction of microbial growth.

Light having wavelengths in a range of about 380-420 nm has been demonstrated to decontaminate the air and exposed surfaces by inactivating microorganisms and pathogens. For purposes of the present disclosure, in some examples, the term "antimicrobial light" includes light within a first wavelength range of about 380-420 nm. In some examples, the antimicrobial light within the first wavelength range has a peak wavelength of about 405 nm. The antimicrobial light has sufficient irradiance (power received by a target surface per unit area) of these wavelengths to result in inactivation of one or more microorganisms at the target surface within a desired period of time. In some examples, antimicrobial light source(s) may include one or more light source elements, such as light-emitting diodes (LEDs), that emit light within the first wavelength range of about 380-420 nm. In some examples, the antimicrobial light within the first wavelength range emitted by the LEDs has a peak wavelength of about 405 nm. It shall be understood that the particular range of wavelengths emitted by the light source element(s) may vary somewhat from these stated ranges, depending, for example, on the response curve for each particular light source element, and the disclosure is not limited in this respect. Also, each light source element does not necessarily emit light across the entire wavelength range. In general, the antimicrobial light contains at least some of these wavelengths at a sufficient intensity to inactivate one or more microorganisms on a target surface within a desired period of time.

In some other examples, the "antimicrobial light" may include light within a second wavelength range, wherein the second wavelength range includes ultraviolet light within a wavelength range of 10-400 nanometers (nm). The ultraviolet light may include ultraviolet A (UVA) light within a wavelength range of 315-400 nm, ultraviolet B (UVB) light within a wavelength range of 280-315 nm and/or ultraviolet C (UVC) light within a wavelength range of 200-280 nm. The intensity of the ultraviolet light has sufficient irradiance (power received by a target surface per unit area) of these wavelengths to result in inactivation of one or more microorganisms at the target surface within a desired period of time. In some examples, the light source elements that emit light within the second antimicrobial wavelength range include light-emitting diodes (LEDs). The light of the first wavelength range and the light of the second wavelength range may be emitted by the same light source elements or by different light source elements.

The spectral energy of the combined antimicrobial light (that is, the light of the first wavelength range combined with the light of the second wavelength range) may be designed such that the proportion of spectral energy of light in the first wavelength range and the proportion of spectral energy within the second wavelength range is optimized with respect to the type of microorganisms targeted, the amount of time required to sufficiently inactivate the targeted microorganisms, to minimize damage such as fading or other degradation of the target surfaces, to minimize human exposure to certain wavelengths of antimicrobial light, the occupancy of the room, and/or other factors which may influence the relative amount of the antimicrobial wavelengths to be applied. For example, in some applications, the combined light may be designed such that at least 30% of the spectral energy of the combined light is within the first wavelength range and at least 30% of the spectral energy of the combined light is within the second wavelength range.

Light elements within the second antimicrobial wavelength range can include light elements that emit one or more of UVA, UVB and/or UVC wavelengths, and these may be used in conjunction with or independently of light elements that emit light within the first antimicrobial wavelength range of 380-420 nm. The light elements of the second antimicrobial wavelength range may be interspersed throughout the array can be activated in such manner that they are cycled sequentially, pulsed independent of the light elements of the first antimicrobial wavelength range, operated at different power settings, etc.

For combined light (that is, the light of the first wavelength range combined with the light of the second wavelength range and the light of the third wavelength range), the proportion of spectral energy of light in the first wavelength range may be such that at least 30% of the spectral energy of the combined light is within the first wavelength range and at least 30% of the spectral energy of the combined light is within the second wavelength range.

An antimicrobial lighting system may include an array of one or more individually controllable antimicrobial light segments. Each antimicrobial light segment may include a substrate and one or more light emitting elements, wherein each of the light emitting elements emits light at a wavelength and irradiance sufficient to inactivate one or more microorganisms on a target surface. For example, an antimicrobial light segment may include an LED light strip including a flexible circuit board or strip populated with multiple surface-mounted LEDs. In other examples, an antimicrobial light segment may include a grid of LEDs printed on a circuit board, panel, or other solid substrate. The substrate may be rigid or flexible, depending upon the needs of the installation. Other examples may include LED tube lights, light bars, rope lights, bulbs, individual light emitting elements, and any other flexible or inflexible light element configuration or shape. The light segments may be customized in size and shape to both fit within the desired spaces within or on the PTAC and to direct light at the wavelength(s) and irradiance at one or more target surfaces within or on the PTAC to achieve a desired level of microbial inactivation at those surfaces, or to reduce or prevent microbial growth at those surfaces, within a desired period of time.

Each individual light element may be directional or omnidirectional. In addition, not all light elements need to have the same directionality; that is, "flood" and "spot" style light elements may be used in the same light segments or through light segments of a lighting array. Individual control of the antimicrobial light segments, or of individual or groups of antimicrobial light source elements within each light segment, may be based on the cycle and/or usage information regarding the PTAC in which in which the antimicrobial light segments are installed, the room or environment in which the PTAC is installed, the type(s) of microorganism(s) to be decontaminated, an amount of time expected to be available for decontamination or an amount of time within which decontamination is desired to occur, the distance between the light source elements and the target surfaces, the time between decontamination events, the amount of soil residue on the target surface(s) and/or other factors that may affect the type and/or amount of antimicrobial light needed to adequately decontaminate the target surfaces within or on the PTAC.

In a PTAC, for example, an antimicrobial lighting system may include an array of one or more individually controllable antimicrobial light segments positioned within the PTAC at identified zones or points of microbial contamination risk, such as at or near the evaporator coils or fins, at or near the condenser coils or fins, at or near the air filter, at or near the air intake or grille, at or near the air discharge grille, within the wall sleeve, around or near the base pan, around or near the compressor, on or near the exterior grille, or any other identified area in or on the PTAC where control of microbial growth is desired.

Each identified target surface or zone within the PTAC is illuminated with light within one or more antimicrobial wavelength range(s) at a sufficient dosage to effect microbial inactivation on identified target surfaces within a desired period of time. The dosage may be defined as the irradiance, or the energy received by a surface per unit area (e.g., as measured in Joules per square centimeter, $J/cm^{-2}$, $W \cdot s \cdot cm^{-2}$) of the antimicrobial wavelength(s) measured at the target surface. The irradiance is dependent at least in part by the power applied to the light source, the distance from the light source to the target surface, the total surface area illuminated, and the time of exposure.

In some examples, an antimicrobial light treatment protocol for a PTAC may be established depending upon the particular installation. For example, it may not be necessary to illuminate all zones or surfaces within or on the PTAC continuously or at the same time or at the same dose. Zones can be treated automatically and selectively by the antimicrobial light when the treatment is most effective or most convenient. In a hotel application, for example, the antimicrobial lighting for a PTAC may be activated when the hotel room in which that PTAC is installed is unoccupied. In another example, the antimicrobial lighting for a PTAC may be manually activated by housekeeping staff during routine cleaning of a room. In another example, the antimicrobial lighting may be manually activated at any time it is determined that the PTAC could benefit from an antimicrobial light treatment. For example, the antimicrobial light treatment could be based on a sensed level of water present in the drip pan. If predetermined amount of water is sensed, the antimicrobial light treatment could be triggered or the dosage of an existing antimicrobial light treatment could be increased. In another example, the antimicrobial lighting may be activated automatically at predefined times of the day, week, or month. In addition, one or more antimicrobial lighting segments may be individually controlled, either manually or automatically, to illuminate only selected zones at certain times. Other zones may not be simultaneously illuminated in order to reduce energy consumption and lengthen LED life.

The antimicrobial light treatment protocol may include a high exposure setting (full power on or highest intensity) antimicrobial cycle mode that occurs when the unit is not in normal use (when a hotel room is unoccupied, for example) as well as a treatment interrupt mode (power down) for power savings or to minimize exposure risk (for example, when a machine is being serviced). The antimicrobial light treatment protocol may also include a reduced power mode or modified setting in which certain antimicrobial light segments are selectively controlled to output a reduced intensity, but at a level that is sufficient to inactivate one or more microorganisms at the target surface(s). For example, the antimicrobial light elements could be cycled in a "race" mode such that light elements will cycle sequentially throughout the array.

The antimicrobial lighting systems may include lighting segments and/or lighting elements that output light within one or more antimicrobial wavelength range(s). For example, some lighting segments or lighting elements may output light within a first antimicrobial wavelength range and some lighting segments or lighting elements may output light within a second antimicrobial wavelength range.

An antimicrobial light array may be installed in the PTAC in such a manner that there is overlapping illumination from each successive lighting element at the target surface at which microbial inactivation is desired. This cone of illumination illuminates a surface area dependent upon the design and physical arrangement of the individual light elements in each lighting segment and the distance of the element(s) from the target surface. The design and installation of the light array will be such that there is continuous or intermittent illumination at the surface throughout the target surface being treated. It shall be understood that the irradiance power at the surface being treated is dependent upon the distance between the emitter and the surface. The power of the antimicrobial light shall be controlled such that sufficient irradiance required for microbiological mitigation within the desired time period is achieved. It shall further be understood that the time/irradiance/distance power relationship required for microbiological mitigation depends upon the target organism(s).

LED lifetime of the antimicrobial lighting elements can range from hundreds to in excess of 100,000 hours of operation. Furthermore, the emitted power of the lamp can be modulated using a Pulse-Width-Modulation (PWM) technique to achieve higher irradiant power without stressing the antimicrobial light to the extent that the light's lifetime is adversely affected when operated under constant power. The frequency and duty cycle applied to the antimicrobial light segments may be modulated to achieve the desired irradiance power at the target surface(s). PWM enables the color temperature (spectral distribution) of the LED lamp to be maintained while varying the observed lamp brightness.

Environmental microorganisms that may be found in or PTAC and other heating and/or air conditioning units and that may be inactivated using the decontamination devices and methods of the present disclosure include, but are not limited to, environmental microorganisms such as *Listeria monocytogenes, Legionella* sp., *Salmonella, Acremonium* sp., *Eurobasidium* sp., *Exophiala* sp., *Sporobolomyces* sp., *Rhodotorula* sp., and the like, varieties of fungus, algae, mold and/or slime, and/or any other pathogen or microorganism that may be encountered on such common touch surfaces.

As one example, FIG. 1 shows an exploded schematic diagram of an example PTAC 10 with antimicrobial light segments 50A-50H installed for inactivation of one or more microorganisms at one or more target surfaces within PTAC 10. Such microbial inactivation may help to reduce or mitigate the growth of one or more microorganisms within or on PTAC 10 and may further help to extend the amount of time between PTAC cleaning protocols.

PTAC 10 includes a wall sleeve 14, an outdoor grille 12, a PTAC unit 16, and a front grille 18. To install PTAC 10, a framed opening sized to receive wall sleeve 14 is prepared in an exterior wall, and wall sleeve 14 is mounted within the framed opening. PTAC 10 is then installed into wall sleeve 14, with the front grille facing the interior of the room and the outside grille facing the exterior of the building.

One or more antimicrobial lighting segments 50, in this example antimicrobial lighting segments 50A-50H, are installed within PTAC 10 to reduce or mitigate microbial growth on one or more target surfaces within or on PTAC 10. For example, one or more antimicrobial light segments 50 may be installed so as to direct antimicrobial light within one or more antimicrobial wavelength range(s) and having sufficient irradiance to result in inactivation of one or more microorganisms at one or more target surfaces within or on PTAC 10 within a desired period of time. Although a specific installation of antimicrobial lighting segments 50A-50H is shown in the example of FIG. 1, it shall be understood that any number of antimicrobial lighting segments 50 may be used, and that any one or more the antimicrobial lighting segments 50 may be installed in alternative locations within or on PTAC 10, and that the disclosure is not limited in this respect.

In the example of FIG. 1, antimicrobial lighting segments 50 are implemented using flexible LED light strips. As such, each antimicrobial lighting segment 50 may be cut and/or shaped to fit a target space where the segment is to be installed, and/or to direct antimicrobial light of sufficient irradiance (power received by a target surface per unit area) of these wavelengths to result in inactivation of one or more microorganisms at the target surface within a desired period of time. In another example, some or all of antimicrobial lighting segments 50 may be a grid or array of LED lighting elements surface mounted to a rigid or flexible circuit board. In other examples, some or all of antimicrobial lighting segments 50 could be LED tube lights, light bars, rope lights, bulbs, individual light source elements, and any other flexible or inflexible light element configuration or shape. The light source elements may be LEDs or may be any other light source capable of emitting antimicrobial light as described herein.

FIG. 1 shows multiple antimicrobial lighting segments 50A-50H installed in various locations within PTAC 10. For example, antimicrobial lighting segment 50A is installed to direct antimicrobial light on an interior surface of outside grille 12. Antimicrobial lighting segments 50B, 50C, and 50D are installed on an interior side of a top surface, a sidewall, and a bottom surface of wall sleeve 14 so as to direct antimicrobial light toward at least some of the components of PTAC unit 16. Antimicrobial lighting segment 50E is installed on a front side of PTAC unit 16 so as to direct antimicrobial light toward the evaporator fins and/or coils. Antimicrobial lighting segment 50F is installed under the air discharge louvers of front grille 18 to direct antimicrobial light toward at least some of the components of PTAC unit 16 and/or to the discharge louvers themselves. Antimicrobial lighting segment 50G is installed under the air intake louvers of front grille 18 to direct antimicrobial light toward at least some of the components of PTAC unit 16 and/or to the air intake grille itself. Antimicrobial lighting segment 50H is installed on an interior side of a front grille sidewall to direct antimicrobial light toward at least some of the components of PTAC unit 16 and/or the interior surface(s) of front grille 18. It shall be understood that each of antimicrobial lighting segments 50A-50H may be installed within or on PTAC 10 so as to direct light in one or more directions and/or at one or more antimicrobial wavelengths so as to direct antimicrobial light toward one or more target surfaces within or on PTAC 10.

FIGS. 2A and 2B are more detailed schematic diagrams of an assembled PTAC 10 and PTAC unit 16, respectively, of the example of FIG. 1. Front grille 16 includes air filter(s) 35, an air intake 36, an air discharge 40, one or more vertical air deflectors 42, and a control panel 44. Control panel 44 includes, for example, an on/off switch, a thermostat or temperature control for setting the desired temperature, a mode switch for selecting the mode of operation (e.g., heat, cool, fan only, energy saver, etc.), a switch for controlling the fan speed (e.g., off, low, high, etc.), a timer, and the like.

PTAC unit 16 includes an evaporator 20, evaporator fins 23, evaporator coils 21, a condenser 22, condenser coils 25, a compressor 26, a base pan 28, and a power cord 30. In use, a refrigerant is circulated through condenser 22 and evaporator 20. Condenser 22 is responsible for converting refrigerant gas into liquid form. Compressor 26 compresses the refrigerant gas and pushes it through condenser coils 25. The increased surface area and high pressure within condenser coils 25 rapidly cool the refrigerant, causing it to change from a gas state to a liquid state. After leaving condenser 22, the liquid refrigerant enters the evaporator coils 21, where it changes back to a gaseous form, pulling heat from nearby warm air. This process creates condensation, which PTAC unit 16 collects and removes via drip or base pan 28. The refrigerant then returns to compressor 26 and the cycle begins again. A fan (not shown in FIG. 2A) moves the cooler, drier air into the room through the air discharge vent 40, thus cooling and decreasing humidity in the room.

Presence of moisture inside of the unit may result in undesirable growth of microorganisms within the interior or on the exterior of the PTAC. For example, various microorganisms including, but not limited to, *Listeria monocytogenes, Legionella* sp., *Salmonella, Acremonium* sp., *Eurobasidium* sp., *Exophiala* sp., *Sporobolomyces* sp., *Rhodotorula* sp., and the like, as well as varieties of fungus, algae, mold and/or slime, may accumulate in and around one or more components of PTAC 16, inside the wall sleeve 14, and in or on the front grille 18 or outside grille 12. These microorganisms may result in unpleasant odors associated with the accumulation of mold, slime and/or other microorganisms within or around PTAC 10. In addition, accumulation of microorganisms within PTAC 10 may result in dispersal of microscopic mold spores or other harmful microorganisms throughout the room or other area in which the PTAC is installed. Exposure to mold can lead to numerous health problems, most directly related to the respiratory system, including asthma, runny nose, coughing, dizziness, and/or allergic reactions. Certain molds may also product toxic compounds such as mycotoxins, which can lead to adverse health consequences.

The antimicrobial lighting systems and/or methods of the present disclosure may improve PTAC hygiene and reduce unpleasant odors associated with the accumulation of mold, slime and other microorganisms in and around the PTAC. In some examples, the systems and/or methods may help extend the time needed between PTAC cleaning procedures to maintain microbial growth below acceptable levels.

Each antimicrobial light segment 50 may be individually controllable such that they may be activated and/or deactivated independently of one another. In addition or alternatively, each light source element within each antimicrobial light segment 50 may also be individually controllable such that they may be activated and/or deactivated independently of one another. Antimicrobial light segments 50 emit antimicrobial light within at least one antimicrobial wavelength range and having an irradiance sufficient to inactivate one or more microorganisms at the target surface(s) within or on PTAC 10 within a specified period of time. For example, one or more of antimicrobial light segments 50 may include one or more light source elements that emit antimicrobial light within a first wavelength range of 380-420 nm and having an irradiance sufficient to inactivate one or more microorganisms at the target surface(s) within a specified period of time. In some examples, the light within the first wavelength range has a peak wavelength of about 405 nm. As another example, one or more of antimicrobial light segments 26 may include one or more light source elements that emit antimicrobial light within a second wavelength range, wherein the second wavelength range may include ultraviolet A (UVA) light within a wavelength range of 315-400 nm, ultraviolet B (UVB) light within a wavelength range of 280-315 nm and/or ultraviolet C (UVC) light within a wavelength range of 200-280 nm and having an irradiance sufficient to inactivate one or more microorganisms at the target surface(s) within a specified period of time.

Use of multiple customizable and individually controllable antimicrobial light segments allows for greater distribution and illumination of antimicrobial light to achieve microbial inactivation at almost any target surface associated within or around a PTAC. For example, areas or surfaces that may be shadowed from one antimicrobial light source by presence of components within the PTAC may be illuminated by other antimicrobial light sources strategically placed in and around the interior and/or exterior of the PTAC such that shadowing within the PTAC can be minimized.

It shall be understood that other configurations of antimicrobial light arrays including one or more antimicrobial light segments may be adapted for installation in any type of heating and/or air conditioning unit. For example, although the antimicrobial light segments of FIGS. 1 and 2 are shown as flexible LED light strips, any other type of lighting segment capable of emitting one or more antimicrobial wavelengths may be used. In addition, multiple rigid and/or flexible antimicrobial light segments may be cut, bent, or curved to fit almost any shaped or curved space within or on a PTAC may be assembled together in an array of individually controllable antimicrobial light segments to provide thorough antimicrobial light application to any location where growth of microorganisms is a concern.

Figure 3:
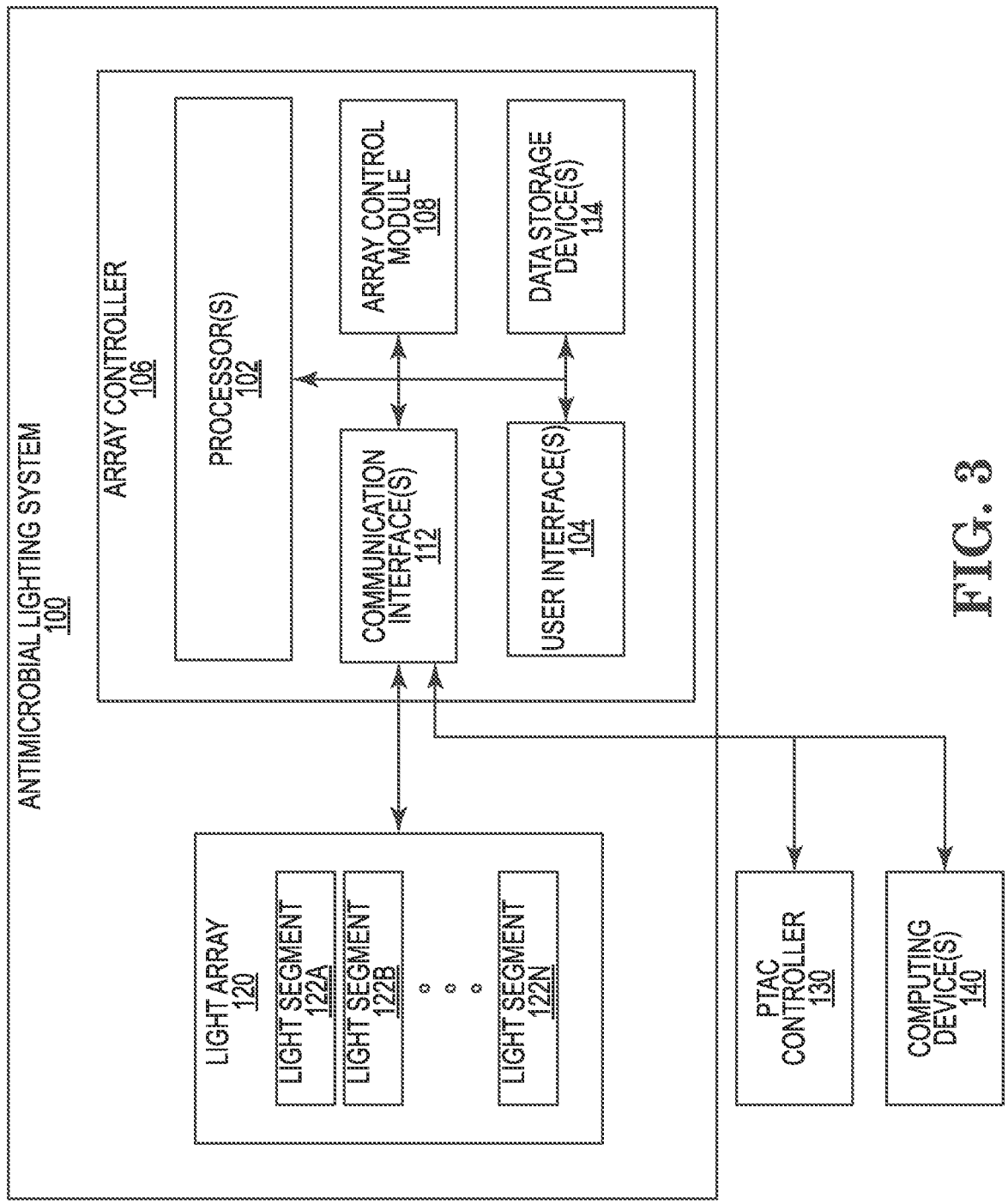
FIG. 3 is a block diagram illustrating an example antimicrobial lighting system including a light array, a light array controller and one or more individually controllable antimicrobial light segments in accordance with the present disclosure.

FIG. 3 is a block diagram illustrating an example antimicrobial lighting system 100 of a type that may be installed to inactivate one or more microorganisms on target surfaces within or on a PAC or other air condition and/or heating unit, or other type of air handling equipment. Antimicrobial lighting system 100 includes a controller 106 and a light array 120 including one or more antimicrobial light segments 122A-122N. Antimicrobial light segments 122A-122N may include any number of segments, and it shall be understood that the disclosure is not limited in this respect. In some examples, antimicrobial light segments 122A-1122N are individually controllable.

In this example, array controller 106 is configured to communicate with a PTAC controller 130. In this way, array controller 106 may receive status information concerning operation of the PTAC and make decisions concerning operation of the antimicrobial light segments 122A-122N based on the PTAC status information. The PTAC status information may be indicative of the current state or cycle of the associated PTAC, such as on, off, cooling, heating, fan setting, or usage information. PTAC status information may further include information from one or more sensors associated with the PTAC including temperature sensors, humidity sensors, and any other sensor associated with the PTAC. The status information may also be indicative of an environmental state inside of the PTAC. For example, if the air space inside a PTAC has become contaminated with particulates that can cause or lead to microbial contamination, and the condition can be detected or sensed, an antimicrobial lighting segment could be activated to remediate that condition. Additional sensor information may include environmental monitoring to indicate conditions of increased microbial activity, such as increased humidity, airborne yeast or mold. The detection of these conditions can indicate that the antimicrobial light power should be increased as a preventative measure against the possible increased microbial activity.

PTAC modes of operation may include a cooling mode, a heating mode, a fan only mode, etc. PTAC usage information may include information concerning the timing, frequency of use, and/or operational mode of the PTAC, which may be indicative of the relative degree of usage of the PTAC. Although a PTAC controller 130 is shown and described for purposes of this example, it shall be understood that antimicrobial lighting system 100 may be configured to communicate with the controller of any other electronically controlled piece of heating and/or air conditioning equipment, and the disclosure is not limited in this respect.

In some examples, each antimicrobial light segment 122A-122N may be implemented using a commercially available LED light strip having a peak wavelength of about 405±5 nm, such as the Single Color Outdoor Weatherproof LED Flexible Light Strip, wavelength 405 nm, Part Number WFLS-UV30, available from Super Bright LEDs Inc., of St. Louis, Missouri, USA (www.superbrightleds.com). These segments are waterproof, flexible, and may be cut to desired lengths for each application, or to fit the intended space within a PTAC (or other piece of heating and/or air conditioning equipment). Each antimicrobial light segment 122A-122N may be adhered to a mounting fixture using an integrated adhesive strip. Each antimicrobial light segment 122A-122N may then be affixed to the desired location within the PTAC using a suitable adhesive or mounting hardware.

Array controller 106 is a computing device that includes one or more processors 102, an array control module 108, one or more user interface components 104, one or more communication components 112, and one or more data storage components 114. User interface components 104 may include one or more of audio interface(s), visual interface(s), and touch-based interface components, including a touch screen, display, speakers, buttons, keypad, stylus, mouse, or other mechanism that allows a person to interact with a computing device. In this example, communication components 112 are configured to communicate control signals from processors 102 to individually control antimicrobial light segments 122A-122N within antimicrobial lighting array 120. Communication components 112 are also configured to receive PTAC status information signals from PTAC controller and transmit the PTAC status information signals to processors 102. The PTAC status information signals are usable by the one or more processors to determine cycle, state, and/or usage information associated with the PTAC. In other examples, communication components 112 may also allow controller 106 to communicate with other remote or local computing devices 135 via wired and/or wireless connections. For example, the remote or local computing devices 135 may include a smart phone, tablet, laptop or other mobile computing device, or a central computing device configured to communicate with and control multiple PTACs located throughout an establishment. In this way, control of the antimicrobial lighting system 100 may be accomplished through computing device(s) 140.

Array control module 108 includes computer readable instructions configured to be executed on the one or more processors 102 to enable controller 106 to individually control activation of antimicrobial light segments 122A-122N of light array 120. For example, array control module 108 may enable controller 100 to individually control activation of antimicrobial light segments 122A-122N based on the status information signals or commands received from PTAC controller 130. In another example, array control module 108 may enable controller 100 to individually control activation of antimicrobial light segments 122A-122N based on the status information signals or commands received from any one of computing device(s) 140. Processor(s) 102 may analyze the received status information signal to determine a current status of the PTAC. For example, one or more of the antimicrobial light segments 122A-122N may be activated to emit antimicrobial light at a first, high setting (that is, a highest intensity) during certain cycles of the PTAC. As another example, one or more of the antimicrobial light segments 122A-122N may be activated to emit antimicrobial light at a second, low setting (that is, relatively lower intensity than the high setting) during certain cycles of the PTAC. As another example, one or more of the antimicrobial light segments 122A-122N may be deactivated so as not to emit antimicrobial light, or be placed in an "off" setting, during certain cycles of the PTAC.

Array control module 108 may also enable controller 106 to individually control activation of antimicrobial light segments 122A-122N based on the time of day. For example, one or more of the antimicrobial light segments 122A-122N may be activated to emit antimicrobial light at a first, high setting (i.e., a highest intensity) during certain defined time periods of the day. As another example, one or more of the antimicrobial light segments 122A-122N may be activated to emit antimicrobial light at a second, low setting (that is, relatively lower intensity than the high setting) during certain defined time periods of the day. As another example, one or more of the antimicrobial light segments 122A-122N may be deactivated so as not to emit antimicrobial light, or be placed in an "off" setting, during certain defined time periods of the day.

In other examples, the antimicrobial light segments 122A-122N may be controlled by array controller 106 such that one or more of the antimicrobial light segments 122A-122N operate at a high setting, one or more of the antimicrobial light segments 122A-122N operate a lower setting (relatively lower than the high setting), and one or more of the antimicrobial light segments 122A-122N are deactivated or turned off. It shall be understood, therefore, that each of the antimicrobial light segments 122A-122N may be individually controlled by array controller 106 to individually active/deactivate and/or adjust the power and/or intensity of the antimicrobial light output by each antimicrobial light segment 122A-122N, and thus to adjust the irradiance of the antimicrobial light received at the target surface(s).

In other examples, the antimicrobial light segments 122A-122N may be controlled by array controller 106 such that one or more of the antimicrobial light segments 122A-122N emit light within a first antimicrobial wavelength range, one or more of the antimicrobial light segments 122A-122N emit light within a second antimicrobial wavelength range, and/or one or more of the antimicrobial light segments 122A-122N are deactivated or turned off. It shall be understood, therefore, that each of the antimicrobial light segments 122A-122N may be individually controlled by array controller 106 to individually control the wavelength of the antimicrobial light output by antimicrobial lighting system 100, and thus to adjust the wavelength(s) of antimicrobial light received at the target surface(s).

Data storage devices 114 of array controller 106 include data received, used or generated by processors 102 during execution of the array control module 108 and/or other functionality of array controller 106. For example, storage components 114 may include any data or cycle signals received from PTAC controller 130, data entered by a user via user interface components 104, data used or generated by array control module 108, or data or commands received from computing device(s) 140.

Antimicrobial lighting system 100 (including array controller 106 and antimicrobial light segments 122A-122N) may include its own internal power supply (such as one or more batteries), or it may be powered from line power (e.g., AC power), such as through a wall outlet. Alternatively, antimicrobial lighting system 100 may be connected to receive power from PTAC controller 130 or from the PTAC unit, thus saving on outlet space.

Antimicrobial light segments 122A-122N may also include one or more LED drivers that are connected to array controller 106 through communication interface(s) 112, and which are configured to individually drive the antimicrobial light segments 122A-122N in response to commands received from array controller 106.

Array control module 108 may include instructions that enable array controller 106 to individually control antimicrobial light segments 122A-122N using one or more settings. For example, the settings may include a high or full power or level setting (e.g., a maximum voltage/current applied), which means that maximum power or level is applied to a selected one or more of the antimicrobial segments 122A-122N. The settings may also include one or more modified power or level settings, such as one or more dimmed settings (e.g., 50% of maximum power, 25% of maximum power, or other selected percentage(s)), which means that the modified power is applied to selected one or more of the antimicrobial light segments. The settings may also include a deactivated setting, in which one or more of the antimicrobial light segments 122A-122N are turned off.

The different level settings correspond to different levels of light output by the antimicrobial light segments 122A-122N. For example, a high or maximum setting corresponds to the highest light output of an antimicrobial light segment (however that maximum may be defined for the system design). A medium or modified setting corresponds to a reduced light output (reduced or lower relative to the high or maximum setting) of an antimicrobial light segment. An "off" setting corresponds to no light output. The medium or modified settings do not necessarily correspond in a linear relationship with the current applied to an antimicrobial light segment, as the response curve of the antimicrobial lights are not necessarily linear with respect to the applied current. In other words, a 50% power applied (compared to a maximum power) does not necessarily result in 50% of maximum light output if the response of the antimicrobial light in questions is not linear. However, it shall be understood that reduced settings correspond to reduced power or current applied, and a reduced light output by the affected antimicrobial light segments.

The antimicrobial light segments 122A-122N are individually controllable by array controller 106 such that they are not all necessarily driven at the same setting(s) at the same time(s). Thus, at any given time, a first selected set of one or more antimicrobial light segment(s) 122A-122N may be driven at first, high, setting, a second selected set of one or more antimicrobial light segment(s) 122A-122N may be driven at a second, modified, setting, and a third selected set of one or more antimicrobial light segment(s) 122A-122N may be deactivated or off.

Antimicrobial lighting system 100 may be controlled through user interface 104 in response to inputs from a user. For example, through the user interface 104, a user may input the desired settings (e.g., high, modified, off, etc.) for some or all of the antimicrobial light segments 122A-122N.

Antimicrobial lighting system 100 may be controlled based on signals received from PTAC controller 130. For example, array control module 108 may analyze the signals received form the PTAC controller 130 to individually control activation of selected antimicrobial light segments 122A-122N at the appropriate setting(s) based on the analysis.

For example, array controller 106 may determine whether to activate one or more of antimicrobial light segments 122A-122N, and determine a power setting at which each light segment 122A-122N should be activated, based on whether the PTAC is operating in a cooling mode, a heating mode, or a fan only mode. As another example, if the PTAC information received from the PTAC controller 130 indicates that the PTAC has been experiencing heavy usage in a cooling mode, array controller 106 may control antimicrobial light segments 122A-122N on a higher power setting as compared to when the PTAC is not experiencing heavy usage in a cooling mode.

Antimicrobial lighting system 100 may be controlled based on the time and/or date. For example, array control module 108 may determine the date and time to determine whether the current time corresponds to a heavy usage time of the PTAC or to a reduced or standby usage time of the PTAC. For example, PTAC units may be used more often in a cooling mode in summer months as compared to winter months, and the likelihood of microbial growth may thus be higher in summer months as compared to winter months.

Antimicrobial lighting system 100 may be controlled based on occupancy of the room. Occupancy may be determined based on a signal received from a door switch or occupancy sensor, or received from one of computing device(s) 140, such as a hotel reservation system. For example, antimicrobial lighting system may be activated when the room is unoccupied and turned off when the room is occupied so as not to distract or annoy guests, or expose them to unnecessary levels of antimicrobial wavelengths.

Antimicrobial lighting system 100 may be manually controlled by a user, such as through user interface 104 or one or more of computing device(s) 140. For example, housekeeping staff may manually activate and/or control antimicrobial lighting system during routine cleaning procedures. As another example, a service technician or custodian may manually activate and/or control antimicrobial lighting system during a service call. As another example, housekeeping, front desk staff, service technician or other authorized user may manually activate antimicrobial lighting system remotely via one or more of computing device(s) 140.

Antimicrobial lighting system 100 may be automatically controlled based on time of day. For example, array control module 108 may determine the time of day and individually control activation of selected antimicrobial light segments 122A-122N based on the time of day. For example, array control module 108 may activate all antimicrobial light segments 122A-122N at a maximum setting upon determining that the time of day and/or date corresponds to a time when the PTAC typically experiences a reduced or no usage level. Array control module 108 may activate selected antimicrobial light segments 122A-122N at a reduced setting (e.g., a lower power or off setting) upon determining that the time and date correspond to a time when the PTAC typically experiences maximum usage levels.

Figure 4:
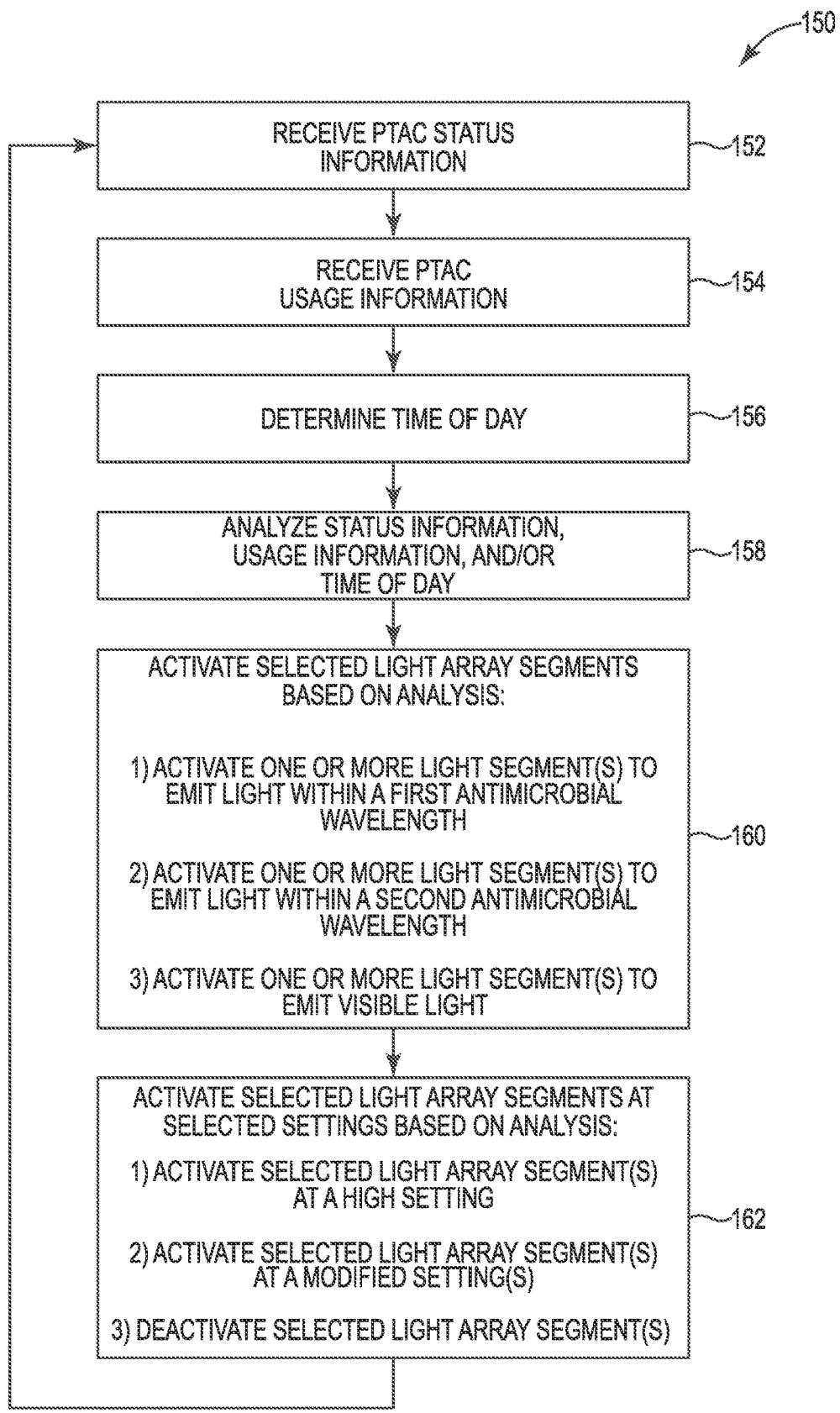
FIG. 4 is a flowchart illustrating an example process by which an array controller may individually control one or more antimicrobial light segments for microbial inactivation on target surfaces in or on a PTAC in accordance with the present disclosure.

FIG. 4 is a flowchart illustrating an example process 150 by which a computing device (such as array controller 106 of FIG. 3) may individually control one or more antimicrobial light segments (such as antimicrobial light segments 122A-122N of FIG. 3) in accordance with the present disclosure. Process (150) will be described with respect application and control of antimicrobial light to achieve microbial inactivation at one or more target surfaces within or on a PTAC; however, it shall be understood that process (150) may apply to application and control of antimicrobial light for microbial inactivation at one or more target surfaces within or on any type of heating and/or air conditioning equipment, and that the disclosure is not limited in this respect.

In the example of FIG. 4, a computing device (such as array controller 106 of FIG. 3) receives PTAC status information (152). For example, the PTAC status information may be received from a PTAC controller, one or more temperature or humidity sensors, a room occupancy sensor, a door sensor, a remote or local computing device, by tapping into the PTAC's fan or condenser actuation signals, or other device capable of communicating PTAC information. The PTAC status information includes information indicative of the current mode, state or cycle of the associated PTAC. The PTAC status may include, for example, information concerning whether the PTAC is operating in a cooling mode, a heating mode, a fan only mode, a sleep mode, or turned off.

The computing device may also receive PTAC usage information (154). For example, the PTAC usage information may be received from a PTAC controller, which may store historical data concerning usage of the PTAC over time. The PTAC usage information may include information indicative of a number air conditioning cycles by day, week or month, settings for each air conditioning cycle, time duration of each air conditioning cycle, and/or a total cumulative usage time. For example, the PTAC usage information may include historical information concerning operation of the PTAC over a period of time, such as dates, cycle on/off times, cycle lengths, temperatures, number of cycles per unit time, indications of when maintenance was performed, indications of one or more malfunctions and the time and date stamp associated with those malfunctions, etc. The computing device may also determine the current time and date (156).

The computing device analyzes the PTAC status information, the PTAC usage information, and/or the current time and date information to determine how to individually control each of the antimicrobial light segments (158). For example, the computing device may activate one or more light segments that emit light within a first antimicrobial wavelength range and/or activate one or more light segments that emit light within a second antimicrobial wavelength range (160). As another example, the computing device may determine that some or all of the antimicrobial light segments should be activated at a high or maximum setting; the computing device may determine that some or all of the antimicrobial light segments should be activated at a modified or reduce setting(s); and/or the computing device may determine that some or all of the light segments should be deactivated (160).

Figure 5A:
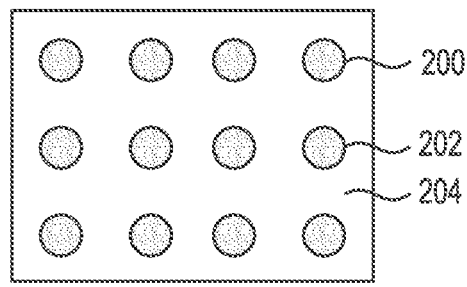
FIGS. 5A and 5B show example grid designs for an antimicrobial light segment.
Figure 5B:
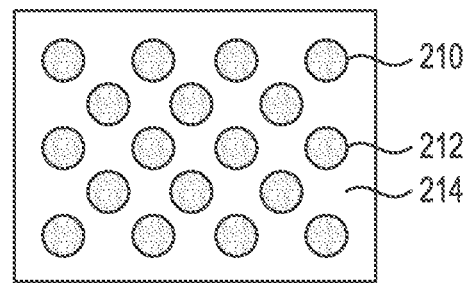

FIGS. 5A and 5B show example antimicrobial light segments 200 and 210, respectively. Each antimicrobial light segment 200, 210 includes a plurality of light source elements 202, 212, arranged in a grid pattern on a substrate 204, 214. The light source elements may be configured in a grid design of suitable dimensions (e.g., length, width, diameter, etc., depending upon the shape) and grid density (the number of light source elements per unit area) to provide sufficient irradiance to achieve inactivation of one or more microorganisms on a target surface within a desired period of time.

Antimicrobial light segment 200 includes a plurality of light source elements, such as light source element 202, arranged in a stacked grid design where each row of light source elements is arranged in line with the light source elements of the adjacent rows. Antimicrobial light segment 210 includes a plurality of light source elements, such as light source element 212, arranged in an offset grid design where each row of light source elements is offset from the light source elements of the adjacent rows. In some examples, an offset grid design such as antimicrobial light segment 210 may enable the light source elements to be packed closer together, thus increasing the density of the light source elements on the substrate. By increasing the density of the light source elements, the amount of light energy impinging on the target surface may be increased. It shall be understood that any suitable arrangement of light source elements on a substrate may be used, and that the disclosure is not limited in this respect.

Figure 5C:
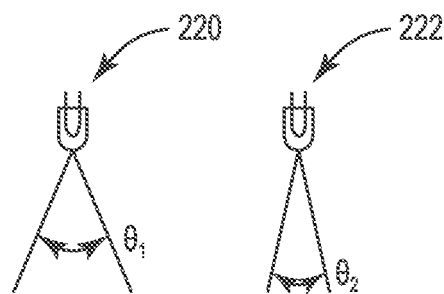
FIG. 5C shows example emission angles for two different LED light source elements.

Light source elements, such as LEDs, are designed to emit light at a known emission angle. The angle is defined as the angle at which the light intensity is 50%. Designing a grid of light source elements based on the emission angle allows the energy impinging upon the target surface to be maximized, for example, when overlapping emission profiles of neighboring elements increase the intensity. FIG. 5C shows two representative emissions angles for a first light source element 220 and a second light source element 222.

In FIG. 5C, the emission angle of light source element 220, $\theta_1$ is relatively greater than the emission angle of light source element 222, $\theta_2$. As a result, in order to achieve overlapping emission, LEDs having a wider emission angle (such as light source element 220) can be relatively further apartment as compared to light source elements having a smaller emission angle (such as light source element 222). The distance between the light source elements and the target surface also affects the emission overlap. These parameters (the emission angle of the light source elements, the distance between the light source elements and/or the density of the light source elements, the distance to the target surface, etc.) can be tailored to maximize the antimicrobial light energy impinging at the target surface. Alternatively, the dimensions can be tailored to achieve a desired amount of antimicrobial light energy impinging at the target surface.

Figure 6:
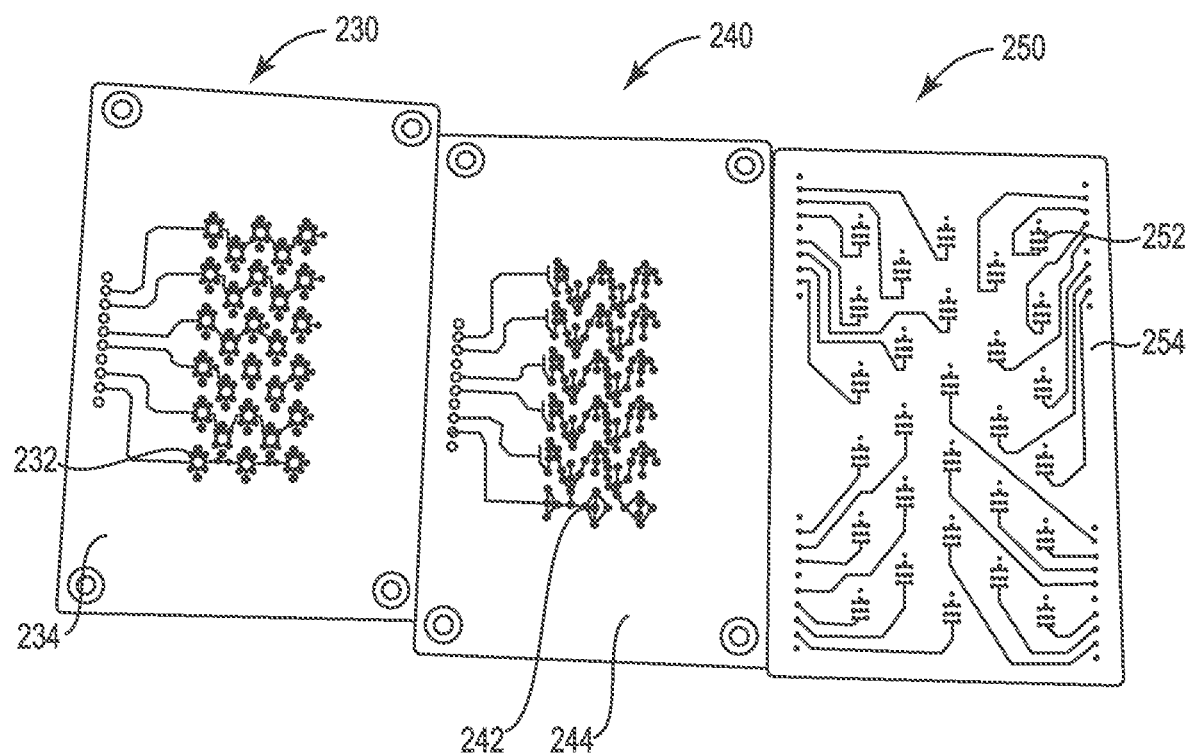
FIG. 6 is a photograph showing two example antimicrobial light segments, each including a plurality of antimicrobial light source elements arranged in grid patterns on a substrate.

FIG. 6 is a photograph showing two example antimicrobial light segments 230 and 250. Each example antimicrobial light segment 230, 250 includes a plurality of antimicrobial light source elements arranged in a grid pattern on a substrate 234, 254, respectively. Circuit board 240 shows the unpopulated circuit board layout of segment 230. In these examples, each antimicrobial light segment includes 28 LED antimicrobial light source elements. Antimicrobial light segment 230/240 has a nominal 0.333-inch spacing and is populated with surface mounted LED light source elements, such as light source element 232. Antimicrobial light segment 250 has a nominal 0.5-inch spacing layout. In these examples, the dimensions of the substrates 234/244, 254 are the same, but the increased distance between light source elements in segment 250 results in a decreased density of light source elements in segment 250 as compared to segment 230/240.

EXAMPLES

Lab experiments to evaluate the antimicrobial effect of antimicrobial light were performed. The irradiance at 405 nm was measured at each of 12 locations on a target surface using a Gentec Pronto-Si laser power meter. The average power across the array was $14.4 \pm 1.1$ mW·cm$^{-2}$. Based on this average power the energy impinging on the sample wells over time was used to calculate antimicrobial light exposure in the sample wells.

| t/min | J·cm$^{-2}$ Gentec |
|---|---|
| 10 | 8.6 |
| 20 | 17.3 |
| 30 | 25.9 |
| 45 | 38.9 |
| 60 | 51.8 |
| 65 | 56.2 |
| 90 | 77.8 |
| 120 | 103.7 |

Results of evaluating/understanding the efficacy of antimicrobial light in liquid media using common organisms in a liquid environment (*Pseudomonas fluorescens, E. coli, Saccharomyces cerevisiae, Candida albicans*) are shown in the following tables:

| Test (antimicrobial test fixture/Liquid media) | | Log (CFU) Survivors/ml | | | | | |
|---|---|---|---|---|---|---|---|
| Tested Organisms | Replicate | After 30 m | After 1 h | After 2 h | After 4 h | After 6 h | After 24 h |
| *E. coli* | R1 | 4.78 | 4.63 | 3.82 | 2.95 | 2.87 | 0.00 |
| *E. coli* | R2 | 4.80 | 4.54 | 3.99 | 3.15 | 2.76 | 0.00 |
| *P. fluorescens* | R1 | 3.34 | 2.48 | 0.00 | 0.00 | 0.00 | 0.00 |
| *P. fluorescens* | R2 | 3.08 | 1.00 | 0.00 | 0.00 | 0.00 | 0.00 |
| *C. albicans* | R1 | 4.72 | 4.84 | 3.84 | 2.92 | 2.79 | 0.30 |
| *C. albicans* | R2 | 4.83 | 4.84 | 3.88 | 2.86 | 2.64 | 0.00 |
| *S. cerevisiae* | R1 | 4.51 | 4.51 | 4.05 | 3.52 | 3.40 | 0.00 |
| *S. cerevisiae* | R2 | 4.61 | 4.58 | 3.91 | 3.60 | 3.32 | 0.00 |

| Control (no light/Liquid media) | | Log (CFU) Survivors/ml | | | | | |
|---|---|---|---|---|---|---|---|
| Tested Organisms | Replicate | After 30 m | After 1 h | After 2 h | After 4 h | After 6 h | After 24 h |
| *E. coli* | R1 | 5.00 | 4.97 | 5.09 | 5.02 | 5.17 | 5.98 |
| *E. coli* | R2 | 5.02 | 5.06 | 4.81 | 5.11 | 5.12 | 5.94 |
| *P. fluorescens* | R1 | 4.85 | 4.82 | 4.92 | 5.04 | 5.11 | 5.10 |
| *P. fluorescens* | R2 | 4.83 | 4.83 | 4.89 | 5.14 | 5.01 | 5.28 |
| *C. albicans* | R1 | 4.75 | 4.61 | 4.67 | 4.95 | 4.92 | 5.84 |
| *C. albicans* | R2 | 4.73 | 4.82 | 4.77 | 4.94 | 4.88 | 5.85 |
| *S. cerevisiae* | R1 | 4.88 | 4.75 | 4.83 | 4.88 | 4.85 | 5.08 |
| *S. cerevisiae* | R2 | 4.90 | 4.72 | 4.81 | 4.90 | 4.91 | 4.76 |

Results of evaluating the efficacy of antimicrobial light on a dried surface (stainless steel coupon) for common organisms (*Pseudomonas fluorescens, E. coli, Candida albicans*) are shown in the following tables:

| Test (antimicrobial test fixture/Stainless steel coupon) | | Log (CFU) Survivors/Carrier | | | |
|---|---|---|---|---|---|
| Tested Organisms | Replicate | After 5.5 h | After 24 h | After 48 h | After 72 h |
| *E. coli* | R 1 | 5.88 | 1.40 | 1.40 | 1.40 |
| *E. coli* | R2 | 5.60 | 1.40 | 1.40 | 1.40 |
| *P. fluorescens* | R 1 | 4.98 | 3.92 | 1.40 | 1.40 |
| *P. fluorescens* | R2 | 5.48 | 1.40 | 1.40 | 1.40 |
| *C. albicans* | R 1 | 4.74 | 2.85 | 1.40 | 1.40 |
| *C. albicans* | R2 | 4.17 | 3.90 | 1.40 | 1.40 |

| Control (no light/Stainless steel coupon) | | Log (CFU) Survivors/Carrier | | | |
|---|---|---|---|---|---|
| Tested Organisms | Replicate | After 5.5 h | After 24 h | After 48 h | After 72 h |
| E. coli | R 1 | 7.27 | 7.28 | 6.94 | 6.43 |
| E. coli | R 2 | 7.27 | 7.30 | 6.99 | 6.28 |
| P. fluorescens | R 1 | 6.93 | 7.14 | 7.16 | 6.02 |
| P. fluorescens | R 2 | 7.02 | 7.15 | 6.69 | 6.29 |
| C. albicans | R 1 | 5.45 | 5.42 | 5.12 | 4.24 |
| C. albicans | R 2 | 5.08 | 5.32 | 5.05 | 5.00 |

Result Discussion

Liquid Media Test Results showed a complete reduction of bacteria and yeast residues in liquid media (from 5 log to zero log) within 24 hours of exposure to antimicrobial light compared to the control result.

Stainless Steel Coupons Test Result showed a complete reduction of bacteria and yeast residues on hard surfaces (from 5 log to 1 log—minimum detectable limit) within 48 hours of exposure to antimicrobial light compared to the control result.

In one or more examples, the functions described may be implemented in hardware, software, firmware, or any combination thereof. If implemented in software, the functions may be stored on or transmitted over as one or more instructions or code on a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transitory media, but are instead directed to non-transitory, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable gate arrays (FPGAs), or other equivalent integrated or discrete logic circuitry. Accordingly, the terms "processor" and "processing circuitry" as used herein may refer to any of the foregoing structures or any other structure suitable for implementation of the techniques described herein. In addition, in some aspects, the functionality described herein may be provided within dedicated hardware and/or software modules configured for encoding and decoding, or incorporated in a combined codec. Also, the techniques could be fully implemented in one or more circuits or logic elements.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a codec hardware unit or provided by a collection of interoperative hardware units, including one or more processors as described above, in conjunction with suitable software and/or firmware.

ADDITIONAL EXAMPLES

Example 1

A system comprising a lighting array including one or more antimicrobial lighting segments, each antimicrobial lighting segment including one or more light source elements, wherein each light source element emits antimicrobial light at a wavelength and irradiance sufficient to inactivate one or more microorganisms on a target surface associated with a heating and/or air conditioning unit; and a lighting array controller comprising: one or more processors; and a data storage device comprising instructions that when executed by the one or more processors cause the one or more processors to: receive one or more signals usable to determine status information concerning the heating and/or air conditioning unit; and individually control each antimicrobial lighting segment based on the determined status information concerning the heating and/or air conditioning unit.

Example 2

The system of Example 1 wherein the status information concerning the heating and/or air conditioning unit includes a current operational mode, and wherein the current operational mode includes one of a cooling mode, a heating mode, a fan only mode, or a sleep mode.

Example 3

The system of Example 1 wherein the heating and/or air conditioning unit is a packaged terminal air conditioner (PTAC).

Example 4

The system of Example 1 wherein the one or more signals usable to determine status information concerning the heating and/or air conditioning unit include a signal indicative of whether the room is occupied.

Example 5

The system of Example 4 wherein the one or more processors individually control each antimicrobial lighting segment based on whether the room is occupied.

Example 6

The system of Example 4 wherein the one or more processors individually control each antimicrobial light segment to emit antimicrobial light when the room is unoccupied.

Example 7

The system of Example 4 wherein the one or more processors deactivate each antimicrobial light segment when the room is occupied.

Example 8

The system of Example 4 wherein the signal indicative of whether the room is occupied is received from a room occupancy sensor or a door sensor.

Example 9

The system of Example 4 wherein the signal indicative of whether the room is occupied is received from a computing device.

Example 10

The system of Example 9 wherein the computing device is a hotel reservation system.

Example 11

The system of Example 1 wherein the one or more processors individually control each antimicrobial light segment based on the determined status information by activating a first set of the antimicrobial lighting segments and deactivating a second set of the antimicrobial lighting segments.

Example 12

The system of Example 1 wherein each of the one or more antimicrobial lighting segments are individually controllable such that each lighting segment may be independently activated at a first, high setting, a second, modified setting, or a third, deactivated setting.

Example 13

The system of Example 1 wherein the one or more antimicrobial lighting segments are disposed within the heating and/or air conditioning unit to direct light at the wavelength and irradiance sufficient to inactivate one or more microorganisms toward one or more target surfaces inside the heating and/or air conditioning unit.

Example 14

The system of Example 1 wherein the target surfaces include one or more of an evaporator coil surface, an evaporator fin surface, a condenser coil surface, an air filter surface, an air intake surface, an air discharge surface, a wall sleeve surface, a base pan surface, a compressor surface, or an exterior grille surface.

Example 15

The system of Example 1 wherein each antimicrobial lighting segment includes a substrate and a plurality of light-emitting diode (LED) elements.

Example 16

The system of Example 1, wherein each antimicrobial lighting segment includes a substrate and a plurality of light-emitting diode (LED) elements, and wherein each LED element emits antimicrobial light within a first wavelength range of about 380-420 nanometers and having a peak wavelength of about 405 nanometers.

Example 17

The system of Example 15, wherein the plurality of LED elements are arranged in a linear pattern on the substrate.

Example 18

The system of Example 15, wherein the plurality of LED elements are arranged in a grid pattern on the substrate.

Example 19

The system of Example 15, wherein the substrate is one of a flexible substrate or a rigid substrate.

Example 20

The system of Example 1, wherein each antimicrobial lighting segment includes a substrate and a plurality of light-emitting diode (LED) elements, wherein one or more of the LED elements emit light within a first antimicrobial wavelength range of about 380-420 nanometers, and one or more of the LED elements emit light within a second antimicrobial wavelength range of about 200-280 nanometers.

Example 21

The system of Example 1, wherein each antimicrobial lighting segment includes a substrate and a plurality of light-emitting diode (LED) elements, wherein one or more of the LED elements emit light within a first antimicrobial wavelength range of about 380-420 nanometers and one or more of the LED elements emit light within a second antimicrobial wavelength range, wherein the second antimicrobial wavelength range includes at least one of ultraviolet A (UVA) light within a wavelength range of 315-400 nm, ultraviolet B (UVB) light within a wavelength range of 280-315 nm or ultraviolet C (UVC) light within a wavelength range of 200-280 nm.

Example 22

A method comprising disposing a lighting array including one or more antimicrobial lighting segments, each antimicrobial lighting segment including one or more light source elements, wherein each light source element emits light at a wavelength and irradiance sufficient to inactivate one or more microorganisms on at least one target surface associated with a heating and/or air conditioning unit; receiving one or more signals usable to determine status information concerning the heating and/or air conditioning unit; and individually controlling each antimicrobial lighting segment based on the determined status information concerning the heating and/or air conditioning unit.

Example 23

The system of Example 22, wherein each antimicrobial lighting segment includes a substrate and a plurality of light-emitting diode (LED) elements, and wherein one or more of the LED elements emit light within a first antimicrobial wavelength range of about 380-420 nanometers and having a peak wavelength of about 405 nanometers.

Example 24

The system of Example 22, wherein each antimicrobial lighting segment includes a substrate and a plurality of light-emitting diode (LED) elements, wherein one or more of the light source elements emit light within a second antimicrobial wavelength range of about 200-280 nanometers.

Various examples have been described. These and other examples are within the scope of the following claims.

The invention claimed is:

1. A system comprising:
a lighting array including one or more antimicrobial lighting segments, each antimicrobial lighting segment of the one or more antimicrobial lighting segments including one or more light source elements configured to emit antimicrobial light at a wavelength and irradiance sufficient to inactivate one or more microorganisms on one or more target surfaces associated with a heating and/or air conditioning unit; and
a lighting array controller comprising:
one or more processors; and
one or more data storages device comprising instructions that when executed by the one or more processors cause the one or more processors to:
receive one or more signals usable to determine status information concerning the heating and/or air conditioning unit, wherein the one or more signals usable to determine the status information concerning the heating and/or air conditioning unit include a signal indicative of whether a room is occupied, wherein the one or more processors are configured to receive the signal indicative of whether the room is occupied from a hotel reservation system; and
individually control each of the one or more antimicrobial lighting segments based on the status information concerning the heating and/or air conditioning unit.

2. The system of claim 1, wherein the status information concerning the heating and/or air conditioning unit includes a current operational mode, and wherein the current operational mode includes one of a cooling mode, a heating mode, a fan only mode, or a sleep mode.

3. The system of claim 1, wherein the heating and/or air conditioning unit is a packaged terminal air conditioner (PTAC).

4. The system of claim 1, wherein the one or more processors are configured to individually control each of the one or more antimicrobial lighting segments based on whether the room is occupied.

5. The system of claim 1, wherein the one or more processors are configured to individually control each of the one or more antimicrobial lighting segments to emit the antimicrobial light when the room is unoccupied.

6. The system of claim 1, wherein the one or more processors are configured to deactivate each of the one or more antimicrobial lighting segments when the room is occupied.

7. The system of claim 1, wherein the one or more processors are configured to receive a second signal indicative of whether the room is occupied from a room occupancy sensor or a door sensor.

8. The system of claim 1, wherein the one or more antimicrobial lighting segments includes a first set of one or more antimicrobial lighting segments and a second set of one or more antimicrobial lighting segments and the one or more processors are configured to individually control each of the one or more antimicrobial lighting segments based on the status information by activating the first set of one or more antimicrobial lighting segments and deactivating the second set of one or more antimicrobial lighting segments.

9. The system of claim 1, wherein each of the one or more antimicrobial lighting segments is individually controllable such that each of the one or more antimicrobial lighting segments is independently activatable at a first setting, a second, modified setting, or a third, deactivated setting.

10. The system of claim 1, wherein the one or more antimicrobial lighting segments are disposed within the heating and/or air conditioning unit to direct the antimicrobial light at the wavelength and irradiance sufficient to inactivate the one or more microorganisms toward the one or more target surfaces, wherein the one or more target surfaces are inside the heating and/or air conditioning unit.

11. The system of claim 1, wherein the one or more target surfaces include one or more of an evaporator coil surface, an evaporator fin surface, a condenser coil surface, an air filter surface, an air intake surface, an air discharge surface, a wall sleeve surface, a base pan surface, a compressor surface, or an exterior grille surface.

12. The system of claim 1, wherein at least one antimicrobial lighting segment of the one or more antimicrobial lighting segments includes a substrate and the one or more light source elements of the antimicrobial lighting segment include a plurality of light-emitting diode (LED) elements on the substrate.

13. The system of claim 12, wherein the plurality of LED elements of the antimicrobial lighting segment are arranged in a linear pattern on the substrate of the antimicrobial lighting segment.

14. The system of claim 12, wherein the plurality of LED elements of the antimicrobial lighting segment are arranged in a grid pattern on the substrate of the antimicrobial lighting segment.

15. The system of claim 12, wherein the substrate is one of a flexible substrate or a rigid substrate.

16. The system of claim 1, wherein at least one antimicrobial lighting segment of the one or more antimicrobial lighting segments includes a substrate and the one or more light source elements of the antimicrobial lighting segment include a plurality of light-emitting diode (LED) elements, and wherein each LED element of the plurality of LED elements is configured to emit the antimicrobial light within a first wavelength range of about 380-420 nanometers and having a peak wavelength of about 405 nanometers.

17. The system of claim 1, wherein at least one antimicrobial lighting segment of the one or more antimicrobial lighting segments includes a substrate and the one or more light source elements of the antimicrobial lighting segment include a plurality of light-emitting diode (LED) elements, wherein one or more of the LED elements are configured to emit a first component of the antimicrobial light within a first antimicrobial wavelength range of about 380-420 nanometers, and one or more of the LED elements are configured to emit a second component of the antimicrobial light within a second antimicrobial wavelength range of about 200-280 nanometers.

18. The system of claim 1, wherein at least one antimicrobial lighting segment of the one or more antimicrobial lighting segments includes a substrate and the one or more light source elements of the antimicrobial lighting segment includes a plurality of light-emitting diode (LED) elements, wherein one or more of the LED elements are configured to emit a first component of the antimicrobial light within a first antimicrobial wavelength range of about 380-420 nanometers and one or more of the LED elements are configured to emit a second component of the antimicrobial light within a second antimicrobial wavelength range, wherein the second antimicrobial wavelength range includes at least one of ultraviolet A (UVA) light within a wavelength range of 315-400 nm, ultraviolet B (UVB) light within a wavelength range of 280-315 nm, or ultraviolet C (UVC) light within a wavelength range of 200-280 nm.

19. A method comprising:

disposing a lighting array including one or more antimicrobial lighting segments, each antimicrobial lighting segment of the one or more antimicrobial lighting segments including one or more light source elements configured to emit antimicrobial light at a wavelength and irradiance sufficient to inactivate one or more microorganisms on at least one target surface associated with a heating and/or air conditioning unit;

receiving, by one or more processors, one or more signals usable to determine status information concerning the heating and/or air conditioning unit, wherein the one or more signals usable to determine the status information concerning the heating and/or air conditioning unit include a signal indicative of whether a room is occupied, wherein the one or more processors are configured to receive the signal indicative of whether the room is occupied from a hotel reservation system; and individually controlling, by the one or more processors, each of the one or more antimicrobial lighting segments based on the status information concerning the heating and/or air conditioning unit.

20. The method of claim 19, wherein at least one antimicrobial lighting segment of the one or more antimicrobial lighting segments includes a substrate and the one or more light source elements of the antimicrobial lighting segment include a plurality of light-emitting diode (LED) elements, and wherein one or more LED elements of the plurality of LED elements are configured to emit the antimicrobial light within a first antimicrobial wavelength range of about 380-420 nanometers and having a peak wavelength of about 405 nanometers.

21. The method of claim 19, wherein at least one antimicrobial lighting segment of the one or more antimicrobial lighting segments includes a substrate and the one or more light source elements of the antimicrobial lighting segment include a plurality of light-emitting diode (LED) elements, wherein one or more of the light source elements are configured to emit the antimicrobial light within a second antimicrobial wavelength range of about 200-280 nanometers.

* * * * *